United States Patent [19]

Hu

[11] Patent Number: 5,256,390
[45] Date of Patent: Oct. 26, 1993

[54] BIOCIDAL ZEOLITE PARTICLES

[75] Inventor: Patrick C. Hu, Baton Rouge, La.

[73] Assignee: Ethyl Corporation, Richmond, Va.

[21] Appl. No.: 548,484

[22] Filed: Jul. 3, 1990

[51] Int. Cl.$^5$ ............................................. C01B 33/34
[52] U.S. Cl. ............................ 423/700; 423/DIG. 24;
502/60; 424/618; 424/630; 424/641
[58] Field of Search ............... 423/118, 326, 328, 329;
502/60, 64; 424/618, 630, 641

[56] References Cited

U.S. PATENT DOCUMENTS 3,382,039 5/1968 Calmon et al. ....................... 502/60
4,330,518 5/1982 Kostinko ............................. 423/328
4,911,899 3/1990 Hagiwara et al. .................. 423/118

OTHER PUBLICATIONS

Masterton et al. "Chemical Principles" 4th Ed. Saunders Co. 1977 p. 473.

*Primary Examiner*—R. Bruce Breneman
*Attorney, Agent, or Firm*—Richard J. Hammond; Terry B. Morris

[57] ABSTRACT

A method of producing zeolite particles with reduced carbonate species so that the zeolite particles are ion exchangeable with biocidal metal ions.

12 Claims, No Drawings

BIOCIDAL ZEOLITE PARTICLES

This invention relates to zeolite particles having biocidal properties and to processes of producing such biocidal zeolite particles. More particularly, the invention relates to the removal of carbonate contaminants in zeolite particles which can result in incomplete ion exchange and/or an unstable end product color. The biocidal zeolite particles produced in accordance with the invention are heat and light color stable. Such zeolite particles have use, among others, as additives to polymeric materials.

BACKGROUND

Certain metal ions are known for having biocidal properties. Transition metal ions, such as silver ions and copper ions, as well as zinc ions, are used for their antibacterial properties. For example, silver ions have been used as a disinfectant or a germicide in the form of a solution of silver nitrate; however, silver nitrate is inconvenient and restrictive in use due to its solution properties. Polymeric materials incorporating such biocidal metal ions are used to avoid the handling problems encountered.

One method of incorporating the metal ions within a polymer is through the dispersion of zeolite particles. In this method the zeolite particles are employed as a carrier for the metal ion. These zeolite particles carrying the biocidal metal ions can be compounded into polymers such as polyethylene, nylon or polyolefin. Such methods are exemplified in Hagiwara et al., U.S. Pat. No. 4,911,899, herein incorporated in its entirety by reference. During the compounding process, these zeolite particles can be exposed to elevated temperatures. The range of temperatures used is dependent on the transition temperature of the polymer used. Such elevated temperatures make heat stable zeolite desirable.

Many methods presently exist for the production of zeolites to be used as biocidal metal ion carriers. Many, if not all, such processes include a step for drying the zeolite particle. One such drying step can be direct drying of the particles with combustion gases. However, such severe drying conditions create zeolite particles upon ion exchange with metal ions form particles which are more easily discolorable when exposed to ultraviolet light and/or elevated temperatures. To avoid such instability, the prior art has moderated such drying conditions, such as by the use of increased air volume in the drying gases. Such steps of moderation increase the length of the time of drying as well as the equipment costs. There continues to be a need for improved methods for the preparation of biocidal zeolite particles.

SUMMARY

Improved processes for preparing biocidal zeolite particles have now been discovered. These processes allow the use of zeolite particles which have been subjected to severe drying conditions without incurring instability of the particles.

DESCRIPTION OF PREFERRED EMBODIMENTS

In one embodiment the present invention is a process for preparing biocidal zeolite particles, which process comprises effectively admixing zeolite particles containing carbonate species with an acidic solution such that at least a significant amount of the carbonate species is converted to a gas. The gas can then be separated from the zeolite particles.

Applicant has discovered that drying zeolite particles (e.g. zeolite A particles) with direct drying results in the association of carbonates, bicarbonates and absorbed carbon dioxide species (all of which are referred to hereinafter as "carbonate species") with the zeolite particles. Direct drying is performed by the combination of fuel and air or other oxygen source. The hot combustion gases then are contacted with the zeolite particles to be dried. The carbon dioxide ($CO_2$) formed in combustion can reacts with causticity in association with the zeolite particles to form carbonate and bicarbonate species. Additionally, formed carbon dioxide can become absorbed into the particle. Applicants have discovered that the association of such carbonate species with zeolite particles can cause the thermal and color instability which the prior art attempts to avoid by use of excess air. Such carbonate species also interfere with ion exchange processes used to impregnate the biocidal metal ions onto the zeolite. Such interference occurs by the formation of complexes such as copper carbonate or silver carbonate.

Further, downstream processes can subject the zeolite particles to an acidic environment. When zeolite particles containing carbonate species are exposed to acid, carbon dioxide gas can be formed and released from the zeolite particles. Such gas cause foaming problems in reactors with resulting overflow or batch size restrictions.

The present invention solves the heretofore unrecognized problem of carbonate species in the zeolite particles by effective processes to remove significant amounts of carbonate species, preferably substantially all.

The zeolite particles to be used in this process for preparing biocidal zeolite particles are any suitable zeolite particles which can be impregnated or loaded with biocidal metal ions. It is intended that this invention be used with such zeolite particles having carbonate species in association with particles. A particular such zeolite is zeolite A particle which have carbonate species that were formed as a consequence of subjecting the particle to drying processes during their manufacture.

The present invention is most optimally used as an intermediate step between the formation of zeolite particle and the ion exchange process intended to impregnate such particles with biocidal metal ions.

The present invention however is not limited to use as an intermediary step. That is, it is used simultaneously with steps to impregnate the zeolite particles with biocidal metal ions. For instance, precipitated zeolite particles having an association with carbonate species can be directly loaded into a solution initially acidic to convert a significant amount of the carbonate species to a gas for venting off. This solution additionally can contain biocidal metal ions which undergo ion exchange with the zeolite particles for impregnation with the biocidal metal ions. For example, a solution of silver nitrate, copper nitrate trihydrate and nitric acid is first formed. A zeolite water slurry is then poured rapidly under vigorous agitation into the vessel containing the prior solution. The new mixture is then permitted to undergo ion exchange for an effective period of time and then the zeolite particles containing the impregnated biocidal metal ions, e.g., silver ions and copper ions, are recovered. Because of the acidic nature of the reaction environment, a significant amount of the carbonate species initially in association with the particles are converted to a gas and vented off. This conversion to a gas occurs very rapidly at the initial stages of the ion exchange process. As a result, the carbonate species are removed before they can interfere with the ion exchange process. Preferably, the solution during the remainder of the ion exchange process is then permitted or forced to undergo an elevation in pH to avoid hydrolysis or protonation of the zeolite.

The biocidal metal ions usable in the present invention are those known in the art, e.g. transitional metal ions, such as silver ions and copper ions, as well as the zinc ions.

In another embodiment of the present invention is a method for producing zeolite A particles suitable for impregnating with biocidal metal ions comprising the step of effectively admixing zeolite particles having one or more carbonate species in association therewith with an acidic solution to remove substantially all of the one or more carbonate species from the particles. In this embodiment, the zeolite particles are those having been created by precipitation from a caustic solution so that one or more carbonate species are in association therewith. Additionally, carbonate species may be present because of a prior drying process. The acidic solution can have a pH of from about 1 to about 7, preferably a pH of about 2. Although the particles can be dried to essentially a bone dry state, it is preferable that zeolite particles after precipitation from the caustic solution retain a water content between the time of precipitation from solution until the admixing of the particles with an acidic solution. Preferably the water content of zeolite particles is at least about one percent by weight. The zeolite particles are admixed with a sufficient volume of acidic solution to effectively remove the carbonate species by the conversion of such species to gases. The acidic solution can comprise an acid selected from sulfuric acid, nitric acid, organic acid and a mixture thereof. The converted gases can be removed from the reaction vessel by venting off, preferably under a controlled vacuum system.

Another embodiment of the present invention is a method for the production of zeolite A particles, the particles comprising carbonate species as an impurity. This method comprises the effective admixing of the particles with an acidic solution to remove a substantial amount of the carbonate species.

In a further embodiment the present invention is a method of producing biocidal zeolite A particles comprising the steps of
  (1) admixing zeolite particles having carbonate species associated therewith with an acidic solution to form a first mixture, this acidic solution being in an effective amount to remove at least a significant amount of a carbonate species, and
  (2) admixing one or more biocidal metal ions with the first mixture to form a second mixture wherein ion exchange occurs to impregnate zeolite particles with the biocidal metal ions,
whereby there is formed biocidal zeolite particles having enhanced heat or color stability.

The present invention permits formation of biocidal zeolite particles with enhanced heat or color stability compared to prior art zeolite particles which have carbonate species in association therewith but which were not treated in accordance with the present invention to remove such carbonate species. As previously discussed, the presence of such carbonate species can interfere with effective ion exchange of biocidal metal ions so as to inhibit impregnation of the zeolite particles with the biocidal metal ions.

Although a significant amount of the carbonated species can be removed in step 1 of the above embodiment by the proper admixing of zeolite particles in an effective amount of the acidic solution, additional acidic solution can be optionally provided during the step 2 admixing of the biocidal metal ions to insure a sufficient removal of carbonate species.

Step 1 of this embodiment can be performed by the quick addition of a first volume of solution comprising the zeolite particles into a second volume of acidic solution. This quick addition is performed under agitation with the second acidic solution volume being substantially greater in volume than the first solution which contains the zeolite particles. This agitation and differences in the volumes are to ensure a quick and thorough contacting of the zeolite particles with an acidic solution. In this quick addition, the first volume of solution can have a pH in excess of 8, preferably a pH of from about 11 to about 12. The pH of the second acidic solution volume can be any acidic pH, preferably a pH of about 2.

During the quick addition, the pH of the admixture must be sufficiently low to effectively convert the carbonate species to a gas. This conversion is a relatively quick reaction. The pH of the admixture is permitted or forced to rise thereafter since the conversion to gases has already occurred. This can be particularly desireable since prolonged exposure of the zeolite particles to an acidic pH can hydrolyze the particles.

The invention will now be described with reference to an illustrative experiment, but is not limited to the example.

Experiment (1) Zeolite A powder was slurried in water to form a slurry fifty weight percent zeolite A.
(2) 4.07 pounds of silver nitrate, 18.97 pounds of copper nitrate trihydrate and 4.4 pounds of nitric acid (active basis) were added to a reactor along with 167 pounds of water.
(3) The zeolite A slurry was poured rapidly into the reactor under vigorous agitation. The reactor mixture was then thermostated to a temperature range of 60° C. to 90° C.
(4) Fifteen minutes after the addition of the zeolite slurry to the reactor, 2.2 pounds of nitric acid was added to the reactor.
(5) The slurry was allowed to undergo ion exchange for about 60–90 minutes.
(6) The slurry was then filtered in a rotary filter and washed with 100–200 pounds of deionized water.
(7) Pan drying of the washed filtrate was done at 105°–150° C. in an oven followed by grinding.

The antibacterial zeolite formed by this process proved to be heat and light color stable.

What is claimed is:

1. A method for producing zeolite A particles suitable for impregnating with biocidal metal ions comprising effectively admixing zeolite particles having one or more carbonate species in association therewith with an acidic solution to remove substantially all of said one or more carbonate species from said particles.

2. The method of claim 1 wherein said zeolite particles having been created by precipitation from a caustic solution so that said one or more carbonate species are in association therewith.

3. The method of claim 1 wherein said acidic solution has a pH of about 2.

4. The method of claim 2 wherein said zeolite particles retain a water content of at least about one percent by weight from the time of said precipitation until said admixing.

5. The method of claim 1 wherein said one or more carbonate species are effectively removed by their conversion to gases.

6. The method of claim 1 wherein said acidic solution comprises an acid selected from sulfuric acid, nitric acid, organic acid and mixtures thereof.

7. A method for the production of zeolite A particles, said particles comprising carbonate species as an impurity, said method comprising the effective admixing of said particles with an acidic solution to remove a substantial amount of said species.

8. A method of producing biocidal zeolite A particles comprising the steps of:

(1) admixing zeolite particles having carbonate species associated therewith with an acidic solution to form a first mixture, said acidic solution being in an effective amount to remove at least a significant amount of said carbonate species, and (2) admixing one or more biocidal metal ions with said first mixture to form a second mixture wherein ion exchange occurs to impregnate said zeolite particles with said biocidal metal ions, whereby there is formed biocidal zeolite particles having enhanced heat or color stability.

9. The method of claim 8 further comprising the admixing of an additional amount of acidic solution during step (2).

10. The method of claim 8 wherein said step (1) is performed by the quick addition of a first volume of solution comprising said zeolite particles into a second volume of acidic solution under agitation, said second volume being substantially greater than said first volume.

11. The method of claim 10 wherein said first volume of solution has a pH of from about 11 to about 12.

12. The method of claim 10 wherein said second volume of acidic solution has a pH of about 2.

* * * * *